US010369055B2

(12) United States Patent
Deisinger et al.

(10) Patent No.: US 10,369,055 B2
(45) Date of Patent: Aug. 6, 2019

(54) MODULAR PATIENT ADAPTER FOR AN EYE LASER DEVICE

(71) Applicant: Novartis AG, Basel (CH)

(72) Inventors: Thomas Deisinger, Erlangen (DE); Daniel Thimm, Erlangen (DE)

(73) Assignee: Novartis AG (CH)

( * ) Notice: Subject to any disclaimer, the term of this patent is extended or adjusted under 35 U.S.C. 154(b) by 162 days.

(21) Appl. No.: 15/246,116

(22) Filed: Aug. 24, 2016

(65) Prior Publication Data

US 2017/0128261 A1     May 11, 2017

(30) Foreign Application Priority Data

Nov. 10, 2015  (EP) .................................... 15003210

(51) Int. Cl.
*A61B 18/20* (2006.01)
*A61F 9/009* (2006.01)
*A61F 9/008* (2006.01)

(52) U.S. Cl.
CPC .......... *A61F 9/009* (2013.01); *A61F 9/00825* (2013.01)

(58) Field of Classification Search
CPC .. A61F 9/009; A61F 2009/0052; A61F 9/008; A61F 9/00802; A61F 9/00821;
(Continued)

(56) References Cited

U.S. PATENT DOCUMENTS 6,623,476 B2 * 9/2003 Juhasz .................... A61F 9/009
606/17
7,955,324 B2 * 6/2011 Melcher .................. A61F 9/009
128/898
(Continued)

FOREIGN PATENT DOCUMENTS

EP         1970034 A1     9/2008
EP         2 057 973 A1 *  5/2009
(Continued)

OTHER PUBLICATIONS

European Search Report; dated May 30, 2016; App. No. 15003210.0; 7 pages.

*Primary Examiner* — Ahmed M Farah
(74) *Attorney, Agent, or Firm* — Keiko Ichiye, Esq.

(57) ABSTRACT

An apparatus for laser assisted eye treatment comprises: a laser device configured to provide focused laser radiation and having an adapter coupling port; an adapter module including first and second sub-modules, the first sub-module configured to detachably couple to the laser device at the adapter coupling port and having a contact surface for an eye, the second sub-module including an eye suction ring portion having a ring axis, wherein the second sub-module delimits at least one suction space, and the adapter module includes a vacuum inlet port in association with each of the at least one suction chamber, wherein the adapter module includes an evacuation path system configured to establish a vacuum communication connection between each of the at least one suction space and the associated vacuum inlet port, wherein the vacuum inlet port is provided at the first sub-module and the evacuation path system extends from the first sub-module to the second sub-module.

12 Claims, 3 Drawing Sheets

(58) Field of Classification Search
CPC .............. A61F 9/00825; A61F 9/00861; A61F 9/0087; A61F 9/00872; A61F 9/00885
USPC ................................................ 606/4, 5, 166
See application file for complete search history.

(56) References Cited

U.S. PATENT DOCUMENTS

| | | | |
|---|---|---|---|
| 8,425,494 B2* | 4/2013 | Muhlhoff | A61F 9/009 414/751.1 |
| 9,968,486 B2* | 5/2018 | Gooding | A61B 3/14 |
| 9,987,165 B2* | 6/2018 | Gooding | A61M 1/0052 |
| 2007/0093795 A1* | 4/2007 | Melcher | A61F 9/009 606/10 |
| 2011/0009851 A1* | 1/2011 | Donitzky | A61F 9/00825 606/4 |
| 2011/0190741 A1* | 8/2011 | Deisinger | A61F 9/00827 606/5 |
| 2012/0016349 A1* | 1/2012 | Brownell | A61F 9/009 606/4 |
| 2012/0083774 A1* | 4/2012 | Robl | A61F 9/009 606/5 |
| 2013/0053837 A1* | 2/2013 | Kandulla | A61F 9/009 606/4 |
| 2016/0106582 A1* | 4/2016 | Campos | A61F 9/009 606/4 |
| 2016/0331586 A1* | 11/2016 | Deisinger | A61F 9/009 |

FOREIGN PATENT DOCUMENTS

| | | | |
|---|---|---|---|
| EP | 2057973 | A1 | 5/2009 |
| WO | 2011/003431 | A1 | 1/2011 |

* cited by examiner

MODULAR PATIENT ADAPTER FOR AN EYE LASER DEVICE

CROSS REFERENCE TO RELATED APPLICATIONS

This application claims priority to European Patent Application Serial Number 15003210.0, filed 10 Nov. 2015, titled "MODULAR PATIENT ADAPTER FOR AN EYE LASER DEVICE," which is hereby incorporated by reference in its entirety.

TECHNICAL FIELD

The present disclosure generally pertains to an adapter module which can be used as a patient adapter to couple an eye to an ophthalmic apparatus.

BACKGROUND

A patient adapter makes it possible to mechanically couple an eye to be treated to a laser apparatus, for example. In this way, the eye can be positioned accurately with respect to the laser apparatus in the direction of propagation of the laser beam emitted by the laser apparatus (this direction is often referred to as a z-direction). In a laser treatment of the eye with the goal of making an incision (cut) in the eye by means of the laser beam, it is necessary to have information of the z-position of the eye in a coordinate system of the laser apparatus. The patient adapter makes it possible to secure the eye in relation to the laser apparatus in the z-direction and thus creates a prerequisite for an accurate application of the incision in the eye in the z-direction.

A conventional example of a patient adapter is designed in two parts and comprises a suction ring and a conical spacer. The suction ring can be placed on the eye and affixed to the eye by suction force. The conical spacer can be coupled to the laser apparatus and has an applanation plate in the region of a narrow cone end. The applanation plate provides a contact surface for the eye and is transmissive for laser radiation. A plurality of suction spaces are at least partially delimited by the suction ring, and a corresponding number of flexible evacuation hoses are provided to connect each suction space with a vacuum pump apparatus. One end of each hose is attached to the suction ring and an opposite end of each hose attached to a connection port at the vacuum pump apparatus. A first of the suction spaces is delimited entirely by the suction ring and is open towards the eye, so that the first suction space can be closed by placing the suction ring on the eye. By subsequently evacuating the first suction space, the suction ring can be affixed to the eye. A second suction space is delimited by both the suction ring and the conical spacer, and evacuation of the second suction space permits to hold the conical spacer in close coupling engagement with the suction ring.

With the conventional patient adapter, the suction ring is initially placed on the eye by the surgeon and is affixed there by applying a vacuum to the first suction space. The conical spacer is in turn mounted on the laser apparatus. In this phase, the suction ring and the spacer are still completely separate from one another. Next, there is a relative approach of the eye with the suction ring sitting on it, on the one hand, and the spacer, which is held on the laser apparatus, on the other hand, until the spacer enters an insertion funnel formed on the suction ring. Finally, a vacuum is created in the second suction space to draw the spacer axially against the suction ring. After bringing the spacer closer to the suction ring by suction, the surface of the eye is leveled off by the applanation plate. In this condition, a cut can be made in the eye tissue, for example, in the cornea, by means of laser radiation of the laser apparatus.

SUMMARY OF THE DISCLOSURE

A drawback of the above conventional solution is that the hoses extending sideward from the suction ring and connected to the vacuum pump apparatus may exert, due to their substantial length and resulting own weight, a pulling or tilting force on the suction ring, at least for as long as the conical spacer is not yet coupled with the suction ring. This force may be felt by the patient as a substantial inconvenience, especially if the hoses are dangling following head movements of the patient. Further, the pulling action of the hoses on the suction ring may be the cause of undesired suction loss in the first suction space.

It is therefore one object of embodiments of the invention disclosed herein to provide a patient adapter which can offer higher convenience for a patient and can better avoid undesired suction loss in a suction space used for affixing a suction ring portion of the adapter to a patient's eye.

According to embodiments, the present disclosure provides an apparatus for laser assisted eye treatment, comprising: a laser device configured to provide focused laser radiation and having an adapter coupling port; an adapter module including first and second sub-modules, the first sub-module configured to detachably couple to the laser device at the adapter coupling port and having a contact surface for an eye, the second sub-module including an eye suction ring portion having a ring axis, wherein the second sub-module delimits at least one suction space, and the adapter module includes a vacuum inlet port in association with each of the at least one suction chamber, wherein the adapter module includes an evacuation path system configured to establish a vacuum communication connection between each of the at least one suction space and the associated vacuum inlet port, wherein the vacuum inlet port is provided at the first sub-module and the evacuation path system extends from the first sub-module to the second sub-module.

In certain embodiments, the evacuation path system includes a hose extending from a hose connection port at the first sub-module to a hose connection port at the second sub-module. The hose may be detachably connected to one or both of the hose connection port at the first sub-module and the hose connection port at the second sub-module. At least one of the hose connection port at the first sub-module and the hose connection port at the second sub-module may be designed as a hose insert.

In certain embodiments, the first sub-module includes a plate portion and the hose connection port at the first sub-module is located at one side of the plate portion. The vacuum inlet port may then be located at an opposite side of the plate portion. A channel may be formed in the plate portion to extend from the one side to the opposite side of the plate portion, and the vacuum inlet port may be formed by an open end portion of the channel located at the opposite side of the plate portion.

In certain embodiments, the adapter coupling port includes a vacuum outlet port and a slide-in structure having at least one slot adapted to slidingly receive in a sliding direction orthogonal to the ring axis a rim portion formed at the first sub-module, wherein the vacuum inlet port moves into overlapping relationship with the vacuum outlet port when the first sub-module is slid into the slide-in structure. In these embodiments, the vacuum outlet port may be formed by a suction cap.

In certain embodiments, the at least one suction space includes a first suction space and a second suction space, and the evacuation path system includes a first hose extending from a first hose connection port at the first sub-module to a first hose connection port at the second sub-module and a second hose extending from a second hose connection port at the first sub-module to a second hose connection port at the second sub-module, wherein the first hose connection port at the second sub-module is in vacuum communication connection with the first suction space and the second hose connection port at the second sub-module is in vacuum communication connection with the second suction space.

In certain embodiments, the at least one suction space includes a suction space operable to cause the eye suction ring portion to be sucked against the eye. The at least one suction space may additionally include a suction space operable to cause the first sub-module to be sucked against the second sub-module.

In certain embodiments, the first and second sub-modules are held together in a module and are adjustable with respect to each other in the module between a first relative position in which the contact surface assumes a first axial position with respect to the eye suction ring portion and a second relative position in which the contact surface assumes a second axial position with respect to the eye suction ring portion, wherein the first axial position of the contact surface corresponds to a position in which the contact surface is still out of contact with the eye when the eye suction ring portion has been placed on the eye, and the second axial position of the contact surface corresponds to a position in which the contact surface is in shaping contact with the eye when the eye suction ring portion is placed on the eye.

The second sub-module may include a centering portion having a funnel section which tapers in a direction axially toward the suction ring portion, and the first sub-module may include a conical portion adapted for axial insertion into the centering portion. The conical portion is inserted deeper into the centering portion in the second relative position of the first and second sub-modules than in the first relative position. The at least one suction space may include a suction space delimited at least partially by the funnel section and the conical portion.

The present disclosure further provides a method for coupling an eye to an ophthalmic apparatus. The method comprises at least the following steps: providing a laser device; providing an adapter module including first and second sub-modules, the first sub-module having a contact surface for an eye, the second sub-module including an eye suction ring portion delimiting a suction space, wherein the first and second sub-modules are adjustable with respect to each other between at least two relative positions in which the contact surface assumes respective different positions with respect to the eye suction ring portion; coupling the first sub-module to the laser device at a coupling port of the laser device; approaching and aligning the eye suction ring portion with respect to the eye; and generating a vacuum in an evacuation path extending between a vacuum inlet port provided at the first sub-module and the suction space, to thereby affix the eye suction ring portion to the eye by means of suction force.

Embodiments of the present invention can be used in conjunction with a broad variety of ophthalmic laser procedures performed on corneal or other tissue areas of an eye. For example, embodiments of the present invention can be used in laser cutting procedures in which a laser-created cut by itself causes no change in the refractive properties of the eye. For example, this is the case in a LASIK treatment (LASIK: Laser in-situ Keratomileusis), wherein first, by means of a laser beam, a corneal segment on the surface of the eye, which is commonly referred to as a "flap" in the art, is cut open. This segment is then folded over to the side to expose the underlying corneal tissue for a subsequent laser ablation. The cut to prepare the flap by itself does not provide any refraction correction. The goal of a refractive correction is pursued only by removal of stromal tissue by laser ablation.

Embodiments of the present invention can also be used in laser surgical procedures for making refractive corrections in an eye, in which a cutting pattern created in the eye should manifest a refractive effect immediately. One example is intracorneal lenticular extraction, in which a volume of lenticular tissue is excised by making a posterior cut and an anterior cut in the cornea of the eye and then removing the lenticular tissue through an extraction channel. The cavity formed in the cornea as a result of removing this tissue portion causes the area of corneal tissue in front (i.e., in the anterior direction) to collapse into it and thereby alter the refractive properties of the cornea. The position and shape of the corneal tissue portion to be extracted must always be determined individually for each patient. This means that the cuts required for preparation of the corneal lenticule must be created accurately with respect to a reference axis of the eye (for example, the optical axis or visual axis) in the patient's eye. This requires the reference axis of the eye to be aligned in relation to an optical axis of the laser apparatus. To do so, the patient may be instructed to stare at a fixed light, for example, with the eye to be treated.

In certain embodiments, the first and second sub-modules can be mounted together as a module and coupled to the laser device as such module. In these embodiments, it may be possible to emit a fixating beam of light along the ring axis through the contact surface and the eye suction ring portion. While the patient with his eye is brought closer to the module (including the first and second sub-modules) mounted on the laser device, the patient can align his eye with the fixating beam of light. As soon as the eye comes in contact with the eye suction ring portion, the eye suction ring portion can be affixed on the eye by creating a vacuum in a suction space. Good alignment of the eye with an optical axis of the laser device can be achieved in this way. Next, the first and second sub-modules may be transferred from a first relative position to a second relative position to cause a displacement of the contact surface in the direction of the ring axis. This axial displacement may cause a deformation of the surface of the eye into a desired shape.

BRIEF DESCRIPTION OF THE DRAWINGS

Embodiments of the present invention will be explained below in greater detail with reference to the accompanying drawings, in which.

DETAILED DESCRIPTION OF THE DRAWINGS

Figure 1:
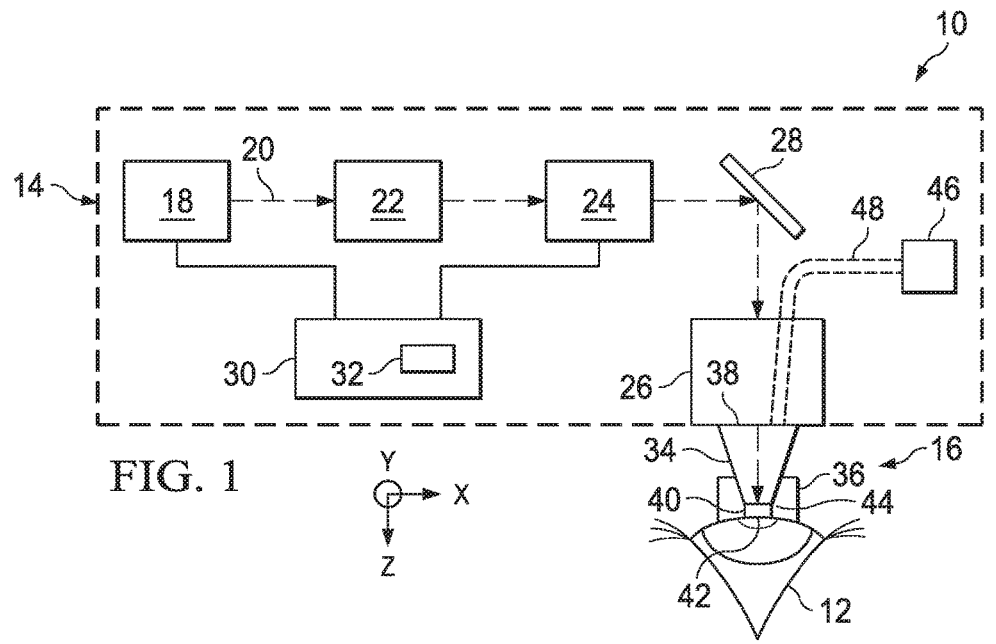
FIG. 1 shows schematically several components of an exemplary embodiment of an eye laser apparatus for laser creation of cuts in eye tissue.

Reference is made first to FIG. 1. The eye laser apparatus shown in a schematic block diagram there is labeled as 10 in general. It is useful for creating cuts in a human eye 12 by means of a laser beam; such cuts are required as part of an intracorneal lenticular extraction, for example. The eye laser apparatus 10 comprises a laser device 14 and an adapter module (patient adapter) 16. The laser device 14 comprises a laser source 18, which generates a beam 20 of ultrashort-pulse laser radiation. The term "ultrashort-pulse" is understood here to refer to pulse durations in the attosecond, femtosecond or picosecond range or, under some circumstances, in the nanosecond range, if other beam parameters have been selected suitably to create a photodisruption based on a laser-induced optical breakdown (LIOB) deep in the tissue of the eye. The wavelength of the laser beam 20 is in a UV range above approx. 300 nm, for example, or in an infrared range, for example, between approx. 800 nm and 1300 nm, so that transmission of the radiation into the eye tissue is ensured.

In the exemplary case shown here, the laser device 14 further comprises a beam-expansion unit 22 formed by a Galilei telescope, for example, that enlarges the beam diameter, a controllable deflector unit 24 (scanner) and a focusing objective 26 for focusing the beam. A stationary beam deflection mirror 28 arranged in the path of the beam between the scanner 24 and the focusing objective 26 is shown in FIG. 1 merely for the sake of the drawing but it need not be provided in a practical embodiment (alternatively, there may be more than one stationary beam deflection mirror in a practical embodiment).

A program-controlled control unit 30 controls the laser source 18 and the scanner 24 in accordance with control commands contained in a control program 32. The control commands define a plurality of shot positions for the laser beam 20, which together represent a cutting pattern to be created in the eye 12. Each shot position represents a point in an xyz-coordinate system of the laser device 14, whose z-axis runs along the direction of the laser beam 20 at the site where the beam exits from the focusing objective 26, and whose x and y-axes span a plane orthogonal to the z-axis. The control unit 30 controls the scanner 24 in such a way that, for each shot position predefined by the control program 32, the beam focus is located at the respective point in the xyz-coordinate system.

The laser device 14 delivers, to the eye tissue to be treated, one or more radiation pulses per shot position, depending on whether the radiation parameters are set for a single pulse application (i.e., a single beam pulse is enough to generate a photodisruption) or a multipulse application (i.e., multiple radiation pulses are necessary to generate a photodisruption).

To adjust the beam focus in the x-direction and in the y-direction, the scanner 24 may comprise, for example, a pair of galvanometrically driven scanner mirrors, which are arranged so that they can be tilted about mutually orthogonal axes of rotation. For controlling the position of the beam focus in the z-direction, the laser device 14 may comprise, for example, a suitable element to influence the divergence of the laser beam 20 before it enters the focusing objective 26. To do so, for example, a lens, which is adjustable in the direction of the beam 20, a lens of variable refractive power or a hollow mirror of variable curvature may be provided.

From a structural standpoint, any such element may be part of the beam-expansion unit 22. It is conceivable, for example, to design an entrance lens, which is itself designed as a divergent lens, of the beam-expansion unit 22 to be adjustable with regard to its position and/or refractive power. Separate diagrams of the beam-expansion unit 22 and of the scanner 24 in FIG. 1 serve only the purpose of illustrating the functional components of the laser device 14 without having to stipulate a certain sequence of different structural components of the laser device 14.

The patient adapter 16 serves to accurately position the eye 12 with respect to the laser device 14 and is made up of a first partial adapter unit (first sub-module) 34 and a second partial adapter unit (second sub-module) 36. The patient adapter 16 is a disposable item, for example, which is used only once and then is either discarded after an operation or is sent to a sterilization station where it is sterilized for possible reuse. The second partial adapter unit 36 is placed on the eye 12 and affixed there by means of a vacuum. The first partial adapter unit 34 is designed for releasable coupling with the laser device 14 underneath the focusing objective 26 at a coupling port generally designated 38 of the laser device 14. The first partial adapter unit 34 has an eye contact element 40, which is transparent, allowing the radiation of the laser beam 20 to propagate through it, and provides a contact surface 42 for the eye 12 on its bottom side, which faces the eye 12.

In the exemplary case shown here the eye contact element 40 is formed by an applanation plate which is designed to be flat on the side facing the eye 12 as well as on the side facing away from the eye. In other embodiments, the eye contact element 40 may have, for example, a concave, convex or otherwise curved contact surface 42 for the eye 12.

The second partial adapter unit 36 includes a centering portion 44 for centering the first partial adapter unit 34 with respect to the second partial adapter unit 36 in an x-y plane. In the z-direction, the first partial adapter unit 34 and the second partial adapter unit 36 can be moved with respect to each other between a first relative position in which the contact surface 42 is still out of contact with the eye 12 when the second partial adapter unit 36 is affixed to the eye 12 and a second relative position in which the contact surface 42 is in shaping contact with the eye 12 when the second partial adapter unit 36 is affixed to the eye 12. In certain embodiments, the first partial adapter unit 34 and the second partial adapter unit 36 are held together in one module and have limited movement play relative to each other in the z-direction in the module. This movement play in the z-direction may be in the range of a few millimeters and may be, for example, no greater than 10 mm or no greater than 8 mm or no greater than 6 mm or no greater than 4 mm. The first and second partial adapter units 34, 36 can be maintained in the second relative position by means of a vacuum. Such vacuum may be generated only after the first and second partial adapter units 34, 36 have been brought into the second relative position or, alternatively, may already be generated before the first and second partial adapter units 34, 36 have reached the second relative position to thereby support or exclusively cause a relative displacement of the two partial adapter units 34, 36 into the second relative position.

In the following, the z-direction is also referred to as an axial direction because in the situation shown in FIG. 1, in which the patient adapter 16 is coupled to the laser device 14, a ring axis (not specifically illustrated in FIG. 1) defined by the second partial adapter unit 36 coincides with the z-direction.

The eye laser apparatus 10 also includes a vacuum source 46 to deliver a vacuum to the first partial adapter unit 34. At least a part of the vacuum delivered to the first partial adapter unit 34 is then delivered from the first partial adapter unit 34 to the second partial adapter unit 36. At least a part of the vacuum delivered to the second partial adapter unit 36 is used to suck the second partial adapter unit 36 against the eye 12. In certain embodiments, a part of the vacuum delivered to the second partial adapter unit 36 is used to suck the first and second partial adapter unit 34, 36 against each other. In other embodiments, a part of the vacuum delivered from the vacuum source 46 to the first partial adapter unit 34 is supplied directly to a sucking space limited between the first and second partial adapter units 34, 36 without being delivered to the second partial adapter unit 36 beforehand.

FIG. 1 schematically shows by way of dashed lines a vacuum supply line 48 extending between the vacuum source 46 and a suitable vacuum inlet port (not shown in FIG. 1) of the patient adapter 16. It should be noted that the patient adapter 16 may be equipped with more than one vacuum inlet port. In this case, each vacuum inlet port of the patient adapter 16 may be connectable or connected via a separate vacuum supply line 48 with the vacuum source 46. In certain embodiments, the patient adapter 16 has two suction spaces, a first for creating a vacuum to suck the second partial adapter unit 36 against the eye 12 and a second to generate a vacuum to suck the first and second partial adapter units 34, 36 against each other. In these embodiments, the patient adapter 16 includes a vacuum inlet port in relation to each of the first and second suction spaces. Two distinct vacuum supply lines 48 extend in these embodiments between the vacuum inlet ports of the patient adapter 16 and the vacuum source 46.

The vacuum source 46 includes, for example, at least one vacuum pump. In certain embodiments, the vacuum source 46 includes a plurality of individually controllable vacuum pumps, each for creating a vacuum in a different suction space of the patient adapter 16.

In the exemplary case shown in FIG. 1, the vacuum source 46 is shown as a component part of the laser device 14. In alternate embodiments, the vacuum source 46 may be a separate component from the laser device 14. Moreover, the vacuum supply line 48 may have a suitable termination element (such as, e.g., a suction cup) that automatically, i.e. without the need for intervention by the surgeon or an assistant, engages in a vacuum-tight manner with a vacuum inlet port of the patient adapter 16 as the latter is mechanically coupled to the laser device 14 at the coupling port 38. In other embodiments, an additional intervention by the surgeon or his assistant may be necessary to establish a vacuum-tight communication connection between the vacuum supply line 48 and a vacuum inlet port of the patient adapter 16 before or after the patient adapter 16 is mechanically coupled to the laser device 14 at the coupling port 38.

For additional details of an exemplary embodiment of the patient adapter 16, reference is now made to the following figures.

Figure 2:
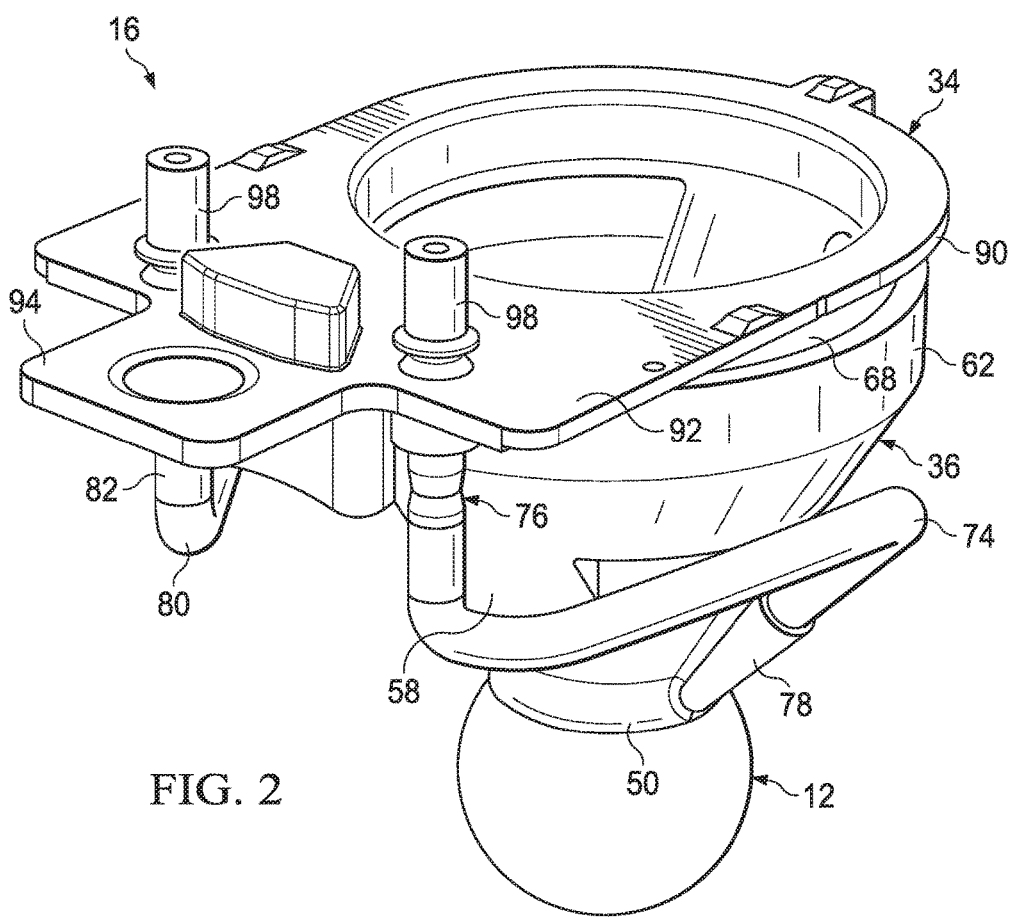
FIG. 2 shows a perspective view of a patient adapter according to one exemplary embodiment.
Figure 3:
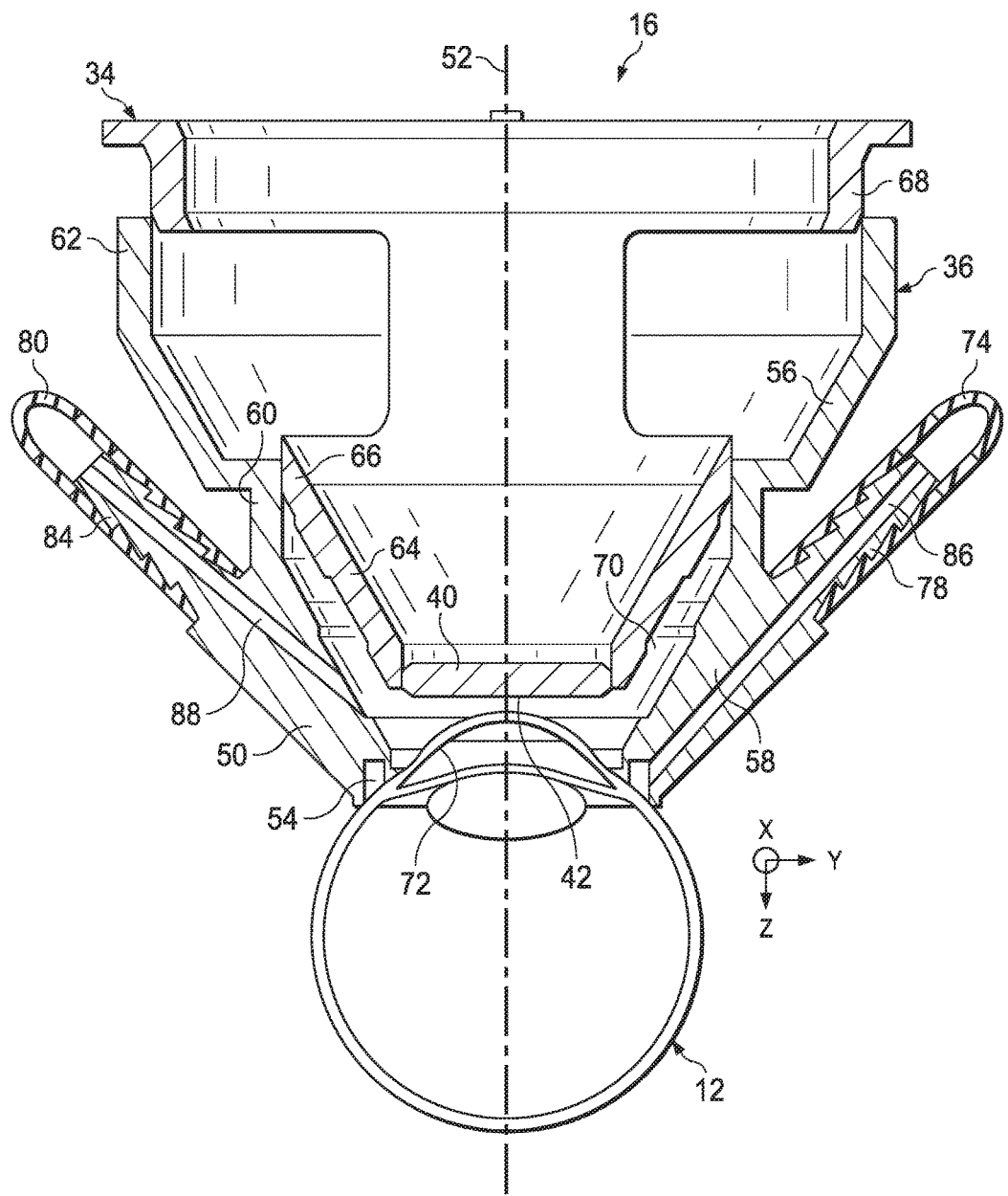
FIG. 3 is a cross-sectional view of the patient adapter of FIG. 2.

FIG. 2 shows a perspective view of a practical implementation of the patient adapter 16 according to an exemplary embodiment. A cross-sectional view of the patient adapter 16 is shown in FIG. 3. As can be seen, the second partial adapter unit 36 comprises a suction ring portion 50 having a ring axis 52 and defining an annular first suction space 54 that opens towards the eye 12 when the suction ring portion 50 is placed onto the eye 12. By evacuating the first suction space 54, the second partial adapter unit 36 can thus be affixed to the eye 12.

The second partial adapter unit 36 further includes a centering portion 56 having a funnel section 58 and cylindrical sections 60, 62. The funnel section 58 tapers in a direction axially toward the suction ring portion 50 and is designed to cooperate with a conical portion 64 of the first partial adapter unit 34. The centering portion 56 of the second partial adapter unit 36 ensures an x-y centration of the first partial adapter unit 34 relative to the second partial adapter unit 36 when the first partial adapter unit 34 is axially inserted in the second partial adapter unit 36. The first partial adapter unit 34 has cylindrical portions 66, 68 dimensioned for axial insertion into the cylindrical sections 60, 62 of the second partial adapter unit 36. More specifically, the cylindrical portion 66 of the first partial adapter unit 34 has an outer diameter corresponding to an inner diameter of the cylindrical section 60 of the second partial adapter unit 36. Further, the cylindrical portion 68 of the first partial adapter unit 34 has an outer diameter corresponding to an inner diameter of the cylindrical section 62 of the second partial adapter unit 36. By engagement of the cylindrical portion 66 in the cylindrical section 60 and engagement of the cylindrical portion 68 in the cylindrical section 62, the first partial adapter unit 34 is therefore centered in an x-y plane relative to the second partial adapter unit 36 without radial play or, alternatively, with little, yet defined radial play.

In the situation shown in FIG. 3, i.e. with the first partial adapter unit 34 axially inserted into the second partial adapter unit 36, a second suction space 70 is delimited between the first partial adapter unit 34, the second partial adapter unit 36 and the eye 12. As can be seen from FIG. 3, a portion of the second suction space 70 extends into a region delimited between the conical portion 64 of the first partial adapter unit 34 and the funnel section 58 of the second partial adapter unit 36.

The first partial adapter unit 34 and the second partial adapter unit 36 are held together in one module, wherein the first partial adapter unit 34 has axial play relative to the second partial adapter unit 36 in the module. For example, one of the first and second partial adapter units 34, 36 may be provided with a plurality of elastically deflectable snap-in tongues (not illustrated in the drawings) by means of which the one of the first and second partial adapter units 34, 36 can be snapped onto the other of the first and second partial adapter units 34, 36. The axial play existing between the first and second partial adapter units 34, 36 permits an axial displacement of the first partial adapter unit 34 relative to the second partial adapter unit 36 between the first relative position, which is shown in FIG. 3, and the second relative position. In the first relative position, the contact element 40, which is carried by the first partial adapter unit 34 in the region of a narrow end of the conical portion 64, is still out of contact with the eye 12. In the second relative position, the first partial adapter unit 34 is inserted maximally deep into the second partial adapter unit 36 in the axial direction; in this position, the contact element 40 presses with its contact surface 42 against the eye 12, deforming a cornea 72 of the eye 12 into a leveled state. By evacuating the second suction space 70, the first and second partial adapter units 34, 36 can be maintained in, and possibly drawn into, the second relative position.

In other embodiments, the first partial adapter unit 34 and the second partial adapter unit 36 may be designed in accordance with the teachings of European patent application no. 15 001 469.4, the content of which is incorporated herein by reference. More specifically, the second partial adapter unit 36 may be comprised of a plurality of components including suction ring member 42, auxiliary member 44 and control ring 46 as shown in FIG. 2 of the mentioned European patent application no. 15 001 469.4.

For the delivery of a vacuum generated by the vacuum source 46 (FIG. 1) to the first suction space 54 and the second suction space 70, the patient adapter 16 includes a first hose (or hose line) 74 extending between a hose connection port 76 and a hose connection port 78 and a second hose (or hose line) 80 extending between a hose connection port 82 and a hose connection port 84. The hose connection ports 78, 84 are provided at the second partial adapter unit 36 and are in vacuum communication connection with the first suction space 54 and the second suction space 70, respectively. As can be seen from FIG. 3, an evacuation path 86 formed in the second partial adapter unit 36 extends from the first suction space 54 to the hose connection port 78. Similarly, an evacuation path 88 extends from the second suction space 70 to the hose connection port 84. The hose connection ports 78, 84 are each designed as a hose insert, so that the hoses 74, 80 can be attached to the second partial adapter unit 36 by slipping a hose end portion onto each of the hose inserts 78, 84.

The hose connection ports 76, 82 are provided at the first partial adapter unit 34 and are each similarly designed as a hose insert. Accordingly, the hoses 74, 80 can be attached to the hose connection ports 76, 82 by slipping an opposite hose end portion onto each of the hose connection ports 76, 82.

As can be particularly seen from FIG. 2, the first partial adapter unit 34 includes a radially projecting flange portion 90 extending over substantially the entire circumference of the first partial adapter unit 34. The flange portion 90 is disposed in the region of an axial end of the first partial adapter unit 34 opposite the contact element 40. In a sub-portion of the circumference of the first partial adapter unit 34, the flange portion 90 is widened out to form a plate portion 92 having a gripping section 94 that facilitates manual handling of the patient adapter 16 during attachment to and release from the coupling port 38. The coupling port 38 may be formed at an output side of the focusing objective 26, i.e. at a side of the focusing objective 26 where the laser beam 20 leaves the objective 26. The coupling port 38 may include one or more coupling structures connected with, or formed on, a housing structure accommodating the optical system of the focusing objective 26. In certain embodiments, the coupling port 38 includes a pair of coupling slots (not shown in the drawings) arranged at a distance from each other and having open slot sides facing each other. These coupling slots define a slide-in structure allowing for sliding insertion of the flange portion 90 into the coupling slots with a sliding motion parallel to an x-y plane. Attachment of the first partial adapter unit 34 to the laser device 14 can thus be effected by inserting the flange portion 90 into the coupling slots and pushing the first partial adapter unit 34 from an insertion-start position to an insertion-end position along an x-y plane wherein the insertion-end position may be defined by one or more stop surfaces (not shown in the drawings) provided by the coupling port 38 in association with each coupling slot.

Figure 4:
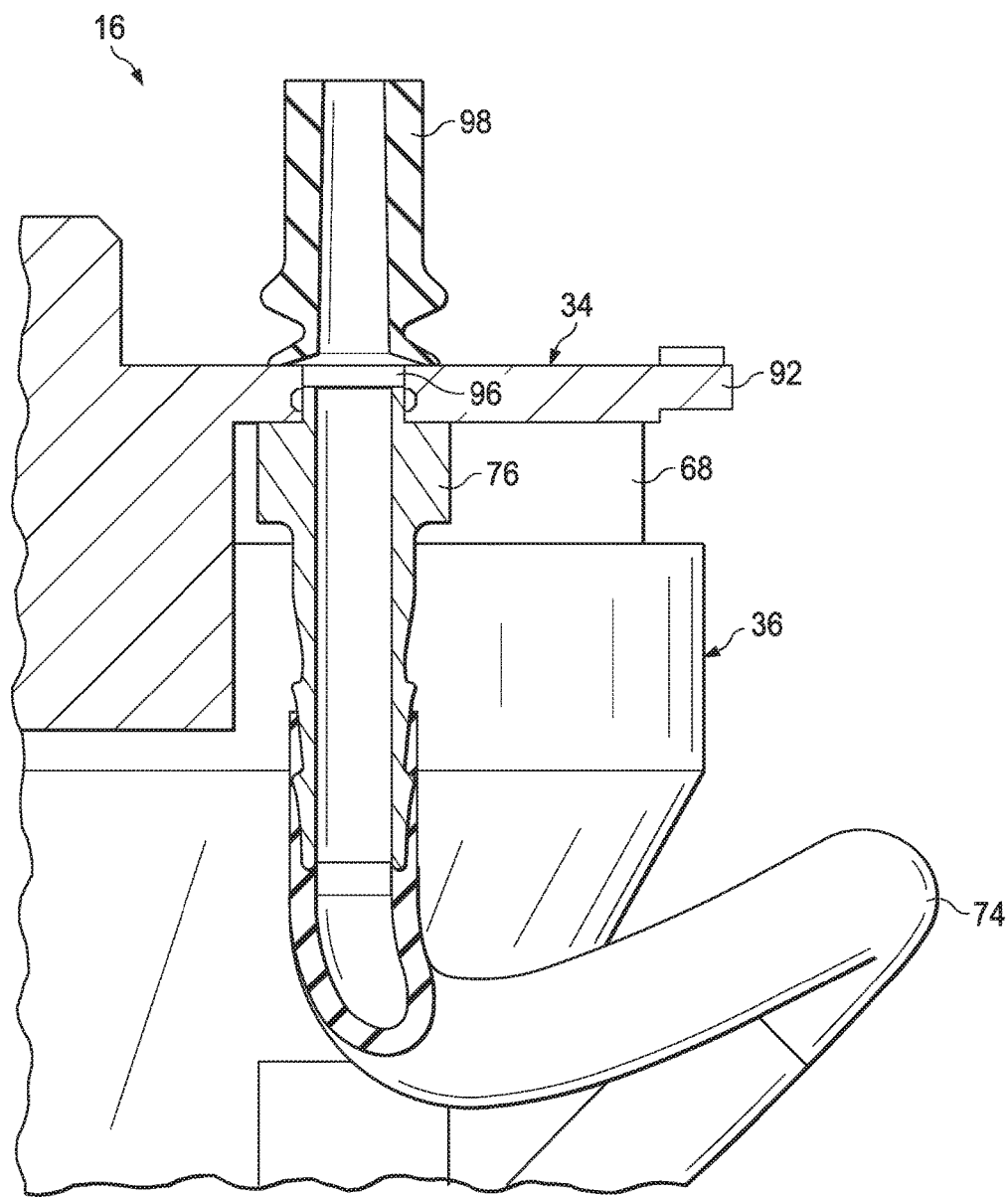
FIG. 4 is a cross-sectional view of a detail of the patient adapter of FIG. 2.

The hose connection ports 76, 82 are arranged at an axial side of the plate portion 92 facing toward the suction ring portion 50 and axially project from this side of the plate portion 92. As can be seen from FIG. 4 for the case of the hose connection port 76, this hose connection port 76 opens into a through-hole 96 formed in the plate portion 92. The through-hole 96 defines a vacuum inlet port of the patient adapter 16, which is located at the opposite axial side of the plate portion 92. A flexible suction cap 98 is disposed at the laser device 14 and forms a vacuum outlet port of the coupling port 38. The suction cap 98 is in alignment with the through-hole 96 and contacts the plate portion 92 around the peripheral edge of the through-hole 96 when the first partial adapter unit 34 is fully coupled to the laser device 14. As the first partial adapter unit 34 is slid into the slide-in structure of the coupling port 38 from the insertion-start position to the insertion-end position, the plate portion 92 moves past the suction cap 98 underneath the same until the through-hole 96 comes into alignment with the suction cap 98. This state corresponds to the insertion-end position of the first partial adapter unit 34. It is to be understood that another through-hole 96 and another suction cap 98 are provided in association with the hose connection port 82.

In other embodiments, which are not particularly illustrated in the drawings, the coupling port 38 is designed to allow for an attachment of the first partial adapter unit 34 to the laser device 14 by approaching the first partial adapter unit 34 to the focusing objective 26 along the z-direction until the first partial adapter unit 34 reaches a coupling position with respect to the focusing objective 26 in which a coupling mechanism becomes active to couple the first partial adapter unit 34 to the focusing objective 26. For example, the coupling mechanism may include one or more snap-in structures formed on at least one of the first partial adapter unit 34 and the focusing objective 26. In these embodiments, no lateral movement of the first partial adapter unit 34 relative to the suction cap 98 is required.

Owing to the presence of the hoses 74, 80, which merely need to bridge a relatively short distance from the first partial adapter unit 34 to the second partial adapter unit 36 and can therefore have a relatively short length, embodiments of the present invention can avoid the use of long hose lines to bridge a long distance from the second partial adapter unit 36 to a vacuum pump mechanism. Embodiments of the present invention can thus offer protection against an undesired suction loss in a suction space used for fixation of a suction ring portion on an eye, which suction loss may come from an undesired dangling or swaying of a hose line.

The invention claimed is:

1. An apparatus for laser assisted eye treatment, comprising:
   a laser device configured to provide focused laser radiation and having an adapter coupling port;
   an adapter module comprising:
      a first sub-module configured to detachably couple to the laser device at the adapter coupling port and having a contact surface for an eye, the first sub-module including a plate portion, a hose connection port at the first sub-module located at one side of the plate portion;
      a second sub-module that includes an eye suction ring portion having a ring axis, and that delimits at least one suction space;
      a vacuum inlet port in association with each of the at least one suction space, the vacuum inlet port located at a side of the plate portion opposite the hose connection port at the first sub-module; and
      an evacuation path system configured to establish a vacuum communication connection between each of the at least one suction space and the associated vacuum inlet port, the vacuum inlet port provided at the first sub-module, the evacuation path system extending from the first sub-module to the second sub-module.

2. The apparatus of claim 1, wherein the evacuation path system includes a hose extending from the hose connection port at the first sub-module to a hose connection port at the second sub-module.

3. The apparatus of claim 2, wherein the hose is detachably connected to at least one of the hose connection port at the first sub-module and the hose connection port at the second sub-module.

4. The apparatus of claim 2, wherein:
at least one of the hose connection port at the first sub-module and the hose connection port at the second sub-module is designed as a hose insert.

5. The apparatus of claim 1, wherein:
a channel is formed in the plate portion to extend from the one side to the opposite side of the plate portion; and
the vacuum inlet port being formed by an open end portion of the channel located at the opposite side of the plate portion.

6. The apparatus of claim 1, wherein the at least one suction space includes a suction space operable to cause the eye suction ring portion to be sucked against the eye.

7. The apparatus of claim 1, wherein the at least one suction space includes a suction space operable to cause the first sub-module to be sucked against the second sub-module.

8. The apparatus of claim 1, wherein:
the first and second sub-modules are held together in a module and are adjustable with respect to each other in the module between a first relative position in which the contact surface assumes a first axial position with respect to the eye suction ring portion and a second relative position in which the contact surface assumes a second axial position with respect to the eye suction ring portion;
the first axial position of the contact surface corresponds to a position in which the contact surface is still out of contact with the eye when the eye suction ring portion has been placed on the eye; and
the second axial position of the contact surface corresponds to a position in which the contact surface is in shaping contact with the eye when the eye suction ring portion is placed on the eye.

9. The apparatus of claim 8, wherein:
the second sub-module includes a centering portion having a funnel section which tapers in a direction axially toward the eye suction ring portion;
the first sub-module includes a conical portion adapted for axial insertion into the centering portion;
the conical portion is inserted deeper into the centering portion in the second relative position of the first and second sub-modules than in the first relative position; and
the at least one suction space includes a suction space delimited at least partially by the funnel section and the conical portion.

10. An apparatus for laser assisted eye treatment, comprising:
a laser device configured to provide focused laser radiation and having an adapter coupling port;
an adapter module comprising:
a first sub-module configured to detachably couple to the laser device at the adapter coupling port and having a contact surface for an eye;
a second sub-module that includes an eye suction ring portion having a ring axis, and that delimits at least one suction space;
a vacuum inlet port in association with each of the at least one suction space; and
an evacuation path system configured to establish a vacuum communication connection between each of the at least one suction space and the associated vacuum inlet port, the vacuum inlet port provided at the first sub-module, the evacuation path system extending from the first sub-module to the second sub-module, wherein:
the adapter coupling port includes a vacuum outlet port and a slide-in structure having at least one slot adapted to slidingly receive in a sliding direction orthogonal to the ring axis a rim portion formed at the first sub-module; and
the vacuum inlet port moves into overlapping relationship with the vacuum outlet port when the first sub-module is slid into the slide-in structure.

11. The apparatus of claim 10, wherein the vacuum outlet port is formed by a suction cap.

12. An apparatus for laser assisted eye treatment, comprising:
a laser device configured to provide focused laser radiation and having an adapter coupling port;
an adapter module comprising:
a first sub-module configured to detachably couple to the laser device at the adapter coupling port and having a contact surface for an eye;
a second sub-module that includes an eye suction ring portion having a ring axis, and that delimits at least one suction space;
a vacuum inlet port in association with each of the at least one suction space; and
an evacuation path system configured to establish a vacuum communication connection between each of the at least one suction space and the associated vacuum inlet port, the vacuum inlet port provided at the first sub-module, the evacuation path system extending from the first sub-module to the second sub-module, wherein:
the at least one suction space includes a first suction space and a second suction space;
the evacuation path system comprises:
a first hose extending from a first hose connection port at the first sub-module to a first hose connection port at the second sub-module; and
a second hose extending from a second hose connection port at the first sub-module to a second hose connection port at the second sub-module;
the first hose connection port at the second sub-module is in vacuum communication connection with the first suction space; and
the second hose connection port at the second sub-module is in vacuum communication connection with the second suction space.

\* \* \* \* \*